US009624313B2

(12) United States Patent
Carvalho Fernandes De Miranda Reis et al.

(10) Patent No.: US 9,624,313 B2
(45) Date of Patent: Apr. 18, 2017

(54) FUCOSE-CONTAINING BACTERIAL BIOPOLYMER

(71) Applicants: Maria D'Ascencao Carvalho Fernandes De Miranda Reis, Lisboa (PT); Rui Manuel Freitas Oliveira, Costa da Caparica (PT); Maria Filomena Andrade De Freitas, Pinhal Novo (PT); Vitor Manuel Delgado Alves, Almada (PT)

(72) Inventors: Maria D'Ascencao Carvalho Fernandes De Miranda Reis, Lisboa (PT); Rui Manuel Freitas Oliveira, Costa da Caparica (PT); Maria Filomena Andrade De Freitas, Pinhal Novo (PT); Vitor Manuel Delgado Alves, Almada (PT)

(73) Assignee: 73100-Setenta E Tres Mil E Cem, LDA, Vila Real (PT)

( * ) Notice: Subject to any disclaimer, the term of this patent is extended or adjusted under 35 U.S.C. 154(b) by 123 days.

(21) Appl. No.: 14/275,776

(22) Filed: May 12, 2014

(65) Prior Publication Data
US 2014/0378556 A1    Dec. 25, 2014

Related U.S. Application Data

(62) Division of application No. 12/968,763, filed on Dec. 15, 2010, now Pat. No. 8,748,123.

(60) Provisional application No. 61/286,687, filed on Dec. 15, 2009.

(51) Int. Cl.
| | | |
|---|---|---|
| C08B 37/00 | (2006.01) |
| A61K 8/73 | (2006.01) |
| A61K 47/36 | (2006.01) |
| A23L 1/054 | (2006.01) |
| C12P 19/04 | (2006.01) |
| A61Q 19/00 | (2006.01) |

(52) U.S. Cl.
CPC .......... *C08B 37/00* (2013.01); *A61K 8/73* (2013.01); *A61K 47/36* (2013.01); *A61Q 19/00* (2013.01); *C12P 19/04* (2013.01); *A23V 2002/00* (2013.01); *A61K 2800/10* (2013.01); *Y10T 428/2982* (2015.01)

(58) Field of Classification Search
CPC ...... C12P 19/04; A23L 1/054; A23V 2001/00; A61K 8/74; A61K 47/36; C08B 37/00; Y10T 428/2982
USPC .............. 514/777; 516/20; 536/123
See application file for complete search history.

(56) References Cited

U.S. PATENT DOCUMENTS

| | | | |
|---|---|---|---|
| 4,298,691 A | 11/1981 | Veeder et al. |
| 4,806,636 A | 2/1989 | Harris et al. |
| 5,876,982 A | 3/1999 | Paul et al. |
| 8,614,070 B2 | 12/2013 | Carvalho Fernandes De Miranda Reis et al. |
| 8,679,796 B2 | 3/2014 | Carvalho Fernandes De Miranda Reis et al. |
| 2002/0115158 A1 | 8/2002 | Yang |
| 2011/0159288 A1 | 6/2011 | Carvalho Fernandes De Miranda Reis et al. |
| 2013/0251806 A1 | 9/2013 | Freitas et al. |

FOREIGN PATENT DOCUMENTS

| | | | |
|---|---|---|---|
| WO | WO 2008/127134 | 10/2008 | |
| WO | WO 2008/127143 A1 * | 10/2008 | ............. C08B 37/00 |

OTHER PUBLICATIONS

Freitas et al, Carbohydrate Polymers, 2009, 78, 549-556.*
Bulk et al, Physiology & Biochemistry, 1991, 81, 619-623.*
Verhoef et al, Biotechnology & Bioengineering, 2005, 91(1), 91-105.*
Baruque-Ramos et al. "Nitrogen consumption during batch cultivation of Neisseria Meniningitidis in frantz medium", Brazilian J of Microbiology, 2001, 32:305-310.
da Paz et al. "Polysaccharide production in batch process of Neisseria Meningitidis serogroup C comparing frantz, modified frantz and catlin 6 cultivation media", Brazilian J of Microbiology, 2003, 34:27-32.
Freitas, F., "Characterization of an Polysaccharide produced by a Psueudomonas strain on Glycerol", Biorsource Technology, 2009, pp. 859-865.
Van Den Bulk, R.W., "Characterization of the Extracellular Polysaccharide produced by *Clavibacter Michiganensis* subsp. *Michiganensis*", Physiology and Biochemistry, 1991, vol. 81, Phythopathology, pp. 619-623.
Vanhooren P.T., Vandamme, E.J., "L-Fucose: occurrence, Physiological role, Chemical, Enzymatic and Microbial Synthesis", J. Chem Technol Biotechnol, 1999, vol. 74, pp. 479-497.
Yang, B.Y., "Extracellular Polysaccharide of Erwinia Chrysanthemi Ech6", Int. J. Biol. Macromol, 1994, vol. 16, pp. 306-312.

(Continued)

*Primary Examiner* — Ganapathy Krishnan
(74) *Attorney, Agent, or Firm* — Gary J. Gershik; Cooper & Dunham LLP

(57) ABSTRACT

The presently disclosed subject matter concerns a microbial biopolymer comprising fucose in its composition. This biopolymer consists of a polysaccharide comprising fucose, which represents at least 10% of its composition. This fucose-containing polysaccharide also contains non-sugar components, namely, acyl group substituents. This disclosed subject matter also concerns the process for the production of the biopolymer, which is obtained cultivation of the bacterium *Enterobacter* A47 (DSM 23139), using glycerol or glycerol-rich mixtures as carbon sources. The fucose-containing biopolymer of the presently disclosed subject matter may be used in several industrial applications (e.g. pharmaceutical, cosmetics and agro-food industries) and in the treatment of industrial wastes (e.g. oil and metal recovery).

17 Claims, 3 Drawing Sheets

(56) References Cited

OTHER PUBLICATIONS

Feb. 5, 2013 Office Action issued in connection with U.S. Appl. No. 12/968,763.
May 6, 2013 Amendment submitted in connection with U.S. Appl. No. 12/968,763.
Jun. 11, 2013 Office Action issued in connection with U.S. Appl. No. 12/968,763.
Dec. 11, 2013 Amendment submitted in connection with U.S. Appl. No. 12/968,763.
Jan. 27, 2014 Amendment submitted in connection with U.S. Appl. No. 12/968,763.
Feb. 5, 2014 Notice of Allowance issued in connection with U.S. Appl. No. 12/968,763.

* cited by examiner

FUCOSE-CONTAINING BACTERIAL BIOPOLYMER

CROSS REFERENCE TO RELATED APPLICATIONS

This application is a divisional of U.S. Ser. No. 12/968,763, filed Dec. 15, 2010, now allowed, which claims the benefit of U.S. Provisional Application No. 61/286,687, filed Dec. 15, 2009, the disclosure of each of which is incorporated herein by reference in its entirety.

FIELD

The disclosed subject matter relates to a microbial biopolymer that contains fucose in its composition. Additionally, the presently disclosed subject matter concerns the process for the production of the fucose-containing biopolymer by the bacterium *Enterobacter* A47 (DSM 23139). Thus, this disclosed subject matter is applicable in several industries (e.g. pharmaceutical, cosmetics and agro-food industries) and in the treatment of industrial wastes (e.g. oil and metal recovery).

BACKGROUND

Polysaccharides are high molecular weight ($10^4$-$10^7$) polymeric biomaterials, formed through the polymerization of monosaccharide repeating units. They possess a great structural diversity as a result of the diversity of the repeating units, type of glycosidic linkages involved and the degree of branching. Many polysaccharides possess non-sugar components, such as organic acyl groups (e.g. acetate, succinate, piruvate) and inorganic groups (e.g. phosphate, sulfate) (Sutherland, 2001).

On the other hand, polysaccharides often form tertiary structures through intra or intermolecular non-covalent linkages, which confer greater rigidity to the macromolecule and play an important role in determining the polymer's properties both in the solid state and in solution (Kumar et al, 2007).

Due to their physical and chemical properties, namely, their water retention ability, rheology and/or film-forming capacity, polysaccharides are used in a wide variety of foods and industrial applications, including textiles, paints, pharmaceuticals and cosmetics, as emulsifying, stabilizing or thickening agents (Moreno et al, 1998). Being materials obtained from living organisms, polysaccharides are usually non-toxic and biodegradable, which makes them biomaterials adequate for sustainable development.

The main applications of commercial polysaccharides, both natural (e.g. alginate, carrageenan, Guar gum, pectins, xanthan, gellan) and semi-synthetic derivatives (e.g. methylcellulose, carboxymethylcellulose, hydroxypropylguar) are based on their ability to modify the physical properties of aqueous systems (hydrocolloids—compounds able to modify the physical properties of aqueous systems), being used mainly in the food industry, followed by the oil and pharmaceuticals industries. Some of these polysaccharides (e.g. alginate, pectins, pullulan, starch derivatives, cellulose derivatives) additionally possess the capacity to form biodegradable films, being used in the manufacturing of packages, vessels and sheets, as well as in several agro-food, pharmaceuticals and industrial applications.

Currently, the majority of the polysaccharides used in industry are obtained from plants (e.g. Guar gum, Arabic gum), algae (e.g. alginate, carrageenan) or crustacean (e.g. chitin), with microbial polysaccharides (e.g. xanthan, gellan, bacterial alginate) representing only a small fraction of the biopolymer's market (Canilha et al, 2005). Nonetheless, in the last years, there has been a growing interest in identifying and isolating new microbial polysaccharides that may compete with the traditional ones, due to their enhanced physical-chemical properties, namely, higher emulsifying and flocculating activities, higher resistance to organic solvents, biological activity (e.g. anticancer or immunoenhancing effects) and better rheological properties (e.g. higher viscosity for lower polymer concentrations, higher stability over wider pH, temperatures and ionic strength ranges) (Kumar et al, 2007; Sutherland, 2001).

Microbial production of polysaccharides has advantages over their extraction from plants, algae or animals, since microorganisms usually exhibit higher growth rates and they are more amenable to manipulation of the cultivation conditions (Moreno et al, 1998). Plants, algae and animals have life cycles of one or more years, being the production cycle usually seasonal. On the other hand, the growth rates of microorganisms is of the order of hours or a few days, while plants, algae and animals have growth rates of the order of months or years.

The main factor limiting the commercial production of microbial polysaccharides is the high substrate cost, mainly sugars, especially glucose, starch and sucrose. In those bioprocesses, substrate cost accounts to 20-40% of the total production costs (Kumar and Mody, 2009).

Hence, the search for less expensive substrates with comparable productivity is essential for the reduction of the production costs. Glycerol, a byproduct of several industrial processes, mainly the biodiesel industry, is a good candidate. Due to the huge growth of the biodiesel industry in the last years, it is being produced in quantities far beyond its current consumption in the traditional glycerol applications. For the biodiesel industry or for any other industry that has glycerol as a byproduct, it represents a burden because of its low commercial value and the fact that its elimination is a cost associated process. Therefore, there is an urgent need for the development of interesting application for this industrial byproduct, making use of the fact that glycerol is a non-toxic and biodegradable compound (Celik et al, 2008).

In addition to their ability to modify the physical properties of aqueous systems, fucose-containing polysaccharides have increased potential for industrial applications due to the fact that fucose is one of the rare sugars, difficult to obtain. On the other hand, the presence of fucose reduces the possibility of allergic reactions, which potentiates the use of these biopolymers in application such as, for example pharmaceuticals and cosmetics.

Fucose may be synthesized through its chemical conversion from other more common monosaccharides, such as galactose or glucose. Nevertheless, most chemical processes are complex, involving several intermediates, and have low yield. An alternative to the chemical synthesis of fucose is the chemical or enzymatic hydrolysis of fucose-containing polysaccharides. These polymers may be found in plants, algae and microorganisms.

In plants, fucose (L-fucose and methylated fucose) occurs, for example, in the cells walls of potato and kiwi fruit, in soybean seeds, in the mucilage of young leaves of *Plantago lanceolata*, in the roots of *Lepidium sativum* and *Glycyrrhiza uralensis*, in the exudates of *Astragalus microcephalus*, *A. gummifer* and *A. kurdicus*, and in the leafs of *Lupinus albus* (Vanhooren e Vandamme, 1999).

In seaweeds, fucose is found in fucoidan that is a homopolysaccharide composed of sulfated L-fucose. Fucose may be extracted from seaweeds such as, for example, *Pelvetia canaliculata, Fucus vesiculosus* and *Ascophyllum nodosum.* In those species, L-fucose content varies between 9.0 and 11.2%. The yield of the global extraction of L-fucose from seaweeds is rather low (around 7.6%) (Vanhooren e Vandamme, 1999).

Several microorganisms, namely, bacteria, fungi and microalgae, synthesize extracellular polysaccharides (EPS) that contain L-fucose. These polymers include both homo and heteropolysaccharides, being the later are more common, containing variable amounts of fucose, as well as other sugar residues (e.g. glucose, galactose, mannose, rhamnose and/or arabinose). L-fucose containing EPS are produced by bacteria belonging to several genera, including *Aerobacter, Azotobacter, Klebsiella, Erwinia, Enterobacter, Pseudomonas, Clavibacter, Bacillus* and *Salmonella,* among others. In fungi, fucose may be found in EPS produced by species belonging to the genera *Candida, Mucor, Polyporus, Rhodotorula e Sporobolomyces,* among others.

In the last decades, the production of L-fucose containing polysaccharides has been reported for several bacterial genera, mainly from the genera *Klebsiella, Enterobacter, Pseudomonas* and *Clavibacter.*

Several *Klebsiella pneumoniae* strains synthesize several different EPS containing L-fucose, D-galactose and galacturonic acid, that differ among them by the degree of acetylation of the polymeric chain. The EPS produced by *K. pneumoniae* 1-1507 (U.S. Pat. No. 5,876,982) has found application in the cosmetics industry due to its psychosensorial qualities, hydrating and self-emulsifying properties (Guetta et al, 2003a). Other EPS possessing a very similar composition, have been described, namely, the EPS produced by *Klebsiella* K-63 (Joseleau and Marais, 1979) and by *K. pneumoniae* ATCC 31646 (U.S. Pat. No. 4,298,691). The polymer of this disclosed subject matter differs from those EPS by the fact that, in addition to fucose and galactose, it also contains glucose. On the other hand, the polymer of this disclosed subject matter has in its composition significant amounts of acyl groups substituents (up to about 25% of the EPS dry weight) that are not referred as components of *Klebsiella* EPS.

*K. pneumoniae* ATCC 12657 (formerly known as *Aerobacter aerogenes* strain A3) produces an EPS composed of fucose, glucose, galactose and glucuronic acid, in approximately equimolar amounts (Vanhooren e Vandamme, 1999). Fucose represents 18.9% of the purified EPS weight (Guetta et al, 2003b). This polysaccharide differs from the polymer of this disclosed subject matter by the high glucuronic acid content, and the presence of acyl groups that are not described for *K. pneumoniae* ATCC 12657 EPS. Moreover, the process described in the presently disclosed subject matter does not use species of the *Klebsiella* genus for the microbial cultivation.

*Enterobacter* strains have also been reported to produce EPS containing fucose, galactose, glucose and glucuronic acid. Examples include: *Enterobacter* sp. CNCM 1-2744 that produces an EPS in which the monomers are present in a ratio of 2:2:1:1 (FR2840920); *Enterobacter* sp. SSYL (KCTC 0687BP) that produces an EPS with a molecular weight between $10^5$ and $10^6$, in which fucose represents 8-10% of the sugar content, being glucuronic acid the main component (40-70%) (US2002115158); and *E. sakazakii,* strains ATCC 53017, ATCC 29004 and ATCC 12868 that produces an EPS with a molecular weight of $2\times10^6$, in which fucose represent 13-22% and mannose content is up to 8%, respectively (U.S. Pat. No. 4,806,636). These polysaccharides differ from the polymer of this disclosed subject matter by the different content of their sugar monomers and acyl groups. Additionally, the polymer of this disclosed subject matter tends to have a typically higher molecular weight in the order of $10^6$-$10^7$.

Several *Clavibacter michiganensis* strains have been described that produce EPS containing L-fucose. Those EPS contain other neutral sugars, such as galactose, glucose and/or mannose, and acyl groups substituents, such as pyruvate, succinate and/or acetate. *C. michiganensis* subsp *michiganensis* Cm 542 (NCPPB 1064) produces a high molecular weight EPS ($10^6$-$10^7$) composed by fucose, galactose and glucose (2:1:1), and pyruvate, succinate and acetate (1:0.5:1.5) (van den Bulk et al, 1991). The polymer of this disclosed subject matter, though possessing a similar composition, differs from *C. michiganensis* EPS by the relative proportion of the acyl groups. The higher succinate content of the polymer of this disclosed subject matter confers it a higher anionic character.

In the document WO2008/127134 a process is described for the production of a galactose-rich polysaccharide by the bacterium *Pseudomonas oleovorans* using glycerol rich substrates. Nevertheless, the EPS obtained in that process contains only residual amounts of fucose (0-4%).

In view of this, the presently disclosed subject matter describes a high molecular weight fucose-containing biopolymer, with a polyelectrolyte character, produced by microbial cultivation, preferably using *Enterobacter* A47 (DSM 23139) and a process thereof. Said process allows obtaining the polymer of the disclosed subject matter using low-cost substrates and in an easy way. The polymer of the disclosed subject matter may be used in several industries, such as agro-food industry, waste water treatment and pharmaceutical industry due to its rehology, film-forming capacity, polyelectrolyte character, and emulsifying flocculating abilities.

General Description of the Disclosed Subject Matter

The presently disclosed subject matter concerns the production of a biopolymer whose main component is a high molecular weight polysaccharide ($10^6$-$10^7$), in which fucose represents at least 10% of its composition, and possessing acyl groups substituents, including pyruvate, succinate and acetate. The biopolymer is obtained by microbial cultivation, preferably by the bacterium *Enterobacter* A47 (DSM 23139) using glycerol or glycerol containing substrates as the preferential carbon sources.

Accordingly, the presently disclosed subject matter provides a process for preparing a polymer comprising the steps of cultivating a microbial culture comprising the bacterial strain *Enterobacter* A47 (DSM 23139) and supplying said culture with a carbon source comprising glycerol.

1. Characterization of the Microbial Culture

The fucose-containing polymer of the presently disclosed subject matter is produced by bacteria of the genera *Pseudomonas, Klebsiella, Methylobacterium, Erwinia, Alcaligenes* or *Enterobacter,* preferably by the bacterium *Enterobacter* A47 deposited Nov. 20, 2009 in DSMZ (Deutsche Sammlung von Mikroorganismen and Zellkulturen GmbH), Inhoffenstr. 7B, D-38124 Braunschweig, Germany, under the Budapest Treaty, with accession number DSM 23139. In addition, the microorganism used in the presently disclosed subject matter is characterized by other aspects, namely, the biochemical profile, genetic sequencing and phylogenetic dendrogram presented in Tables 1 and 2, and FIG. 1, respectively.

The microorganism used in this disclosed subject matter may be a wildtype strain, a variant or a mutant, as long as it possesses the ability to synthesize the fucose-containing polymer. It is possible to use a pure culture or a mixed culture of several microorganisms, among which, at least one is capable of producing the fucose-containing polymer, preferably the bacterium *Enterobacter* A47 (DSM 23139).

2. Characterization of the Process for the Production of the Polymer

The polymer of the presently disclosed subject matter is produced in a bioreactor in a stirred and aerated aqueous medium. The cultivation medium contains a carbon source, a nitrogen source and inorganic salts. The preferential carbon source is glycerol or glycerol containing substrates. Nevertheless, the process for the production of the polymer of the disclosed subject matter foresees the use of other carbon sources, either in alternative to glycerol or in mixture with glycerol, such as for example, sugars, alcohols, organic acids or alkanes, as well as food and industrial wastes or byproducts, such as for example glycerol byproduct from the biodiesel industry, sugar molasses, whey or olive oil production wastes.

The process for the production of the fucose-containing polymer consists on the cultivation of the microorganism in a nutrient aerated aqueous medium. The temperature is controlled between 15 and 45° C., preferably between 26 and 37° C. The pH is controlled between 5.0 and 9.0, preferably between 6.5 and 7.0.

At the beginning of the cultivation, the dissolved oxygen concentration in the cultivation medium is settled above 70%. Afterwards, the dissolved oxygen concentration gradually decreases, concomitant with cell growth, being controlled below 30%, or preferably below 20%, or most preferably below 10% or even in anaerobic conditions. The fucose-containing polymer is produced under conditions of nitrogen limitation, such as in an amount less than 0.3 g/L, or less than 0.2 g/L, or less than 0.1 g/L or even without nitrogen source and carbon availability, simultaneously with low dissolved oxygen concentration, as described above. Carbon availability is guaranteed by supplying the culture with cultivation medium containing a high glycerol concentration (>100 g/L). The flow rate of addition of such a medium during this fed-batch phase must be adjusted to match the culture's carbon consumption.

The culture broth obtained at the end of the cultivation in the bioreactor may be used directly, without any treatment, or after being dried. Alternatively, the fucose-containing polymer may be precipitated from the broth by the addition of a precipitating agent (e.g. ethanol, acetone), yielding a native polymer.

The extraction process of the polymer of the disclosed subject matter consists on cell removal (e.g. by centrifugation of the broth), followed by the precipitation of the polymer by addition of a precipitating agent. The purification of the polymer involves the use of one or several additional processes (e.g. dialysis).

Depending of the cultivation conditions in the bioreactor, the cultivation time and the procedures used to extract/purify the polymer, the process yields 50 g/L of native polymer or 20 g/L of purified polymer.

3. Characterization of the Polymer

Typically, the polymer of the disclosed subject matter has a fucose content that represents at least 10% of its sugar composition. The fucose-containing polymer has in its composition other neutral sugars, namely, glucose and galactose, and it may also contain in trace amounts (<5%) other sugars, such as for example mannose, rhamnose, arabinose, fructose, glucuronic acid and/or glucosamine.

4. Applications of the Polymer

The polymer of the disclosed subject matter presents flocculating and emulsifying activities, it forms highly viscous aqueous solutions with pseudoplastic fluid behavior, and produces biodegradable films when mixed with other polymers. Hence, it may replace other polysaccharides, such as for example xanthan, alginate, carrageenan, Guar gum and Arabic gum, in their numerous applications, namely, in the agro-food industry, in pharmaceuticals and cosmetics. In addition, the presence of fucose in the polymer of the disclosed subject matter further potentiates its use in medical and cosmetic applications. Moreover, the presence of pyruvate and succinate residues confers an anionic character to the polymer. As a consequence, it is able to immobilize toxic metals.

DETAILED DESCRIPTION OF EXEMPLARY EMBODIMENTS

1. Characterization of the Microorganism

Figure 1:
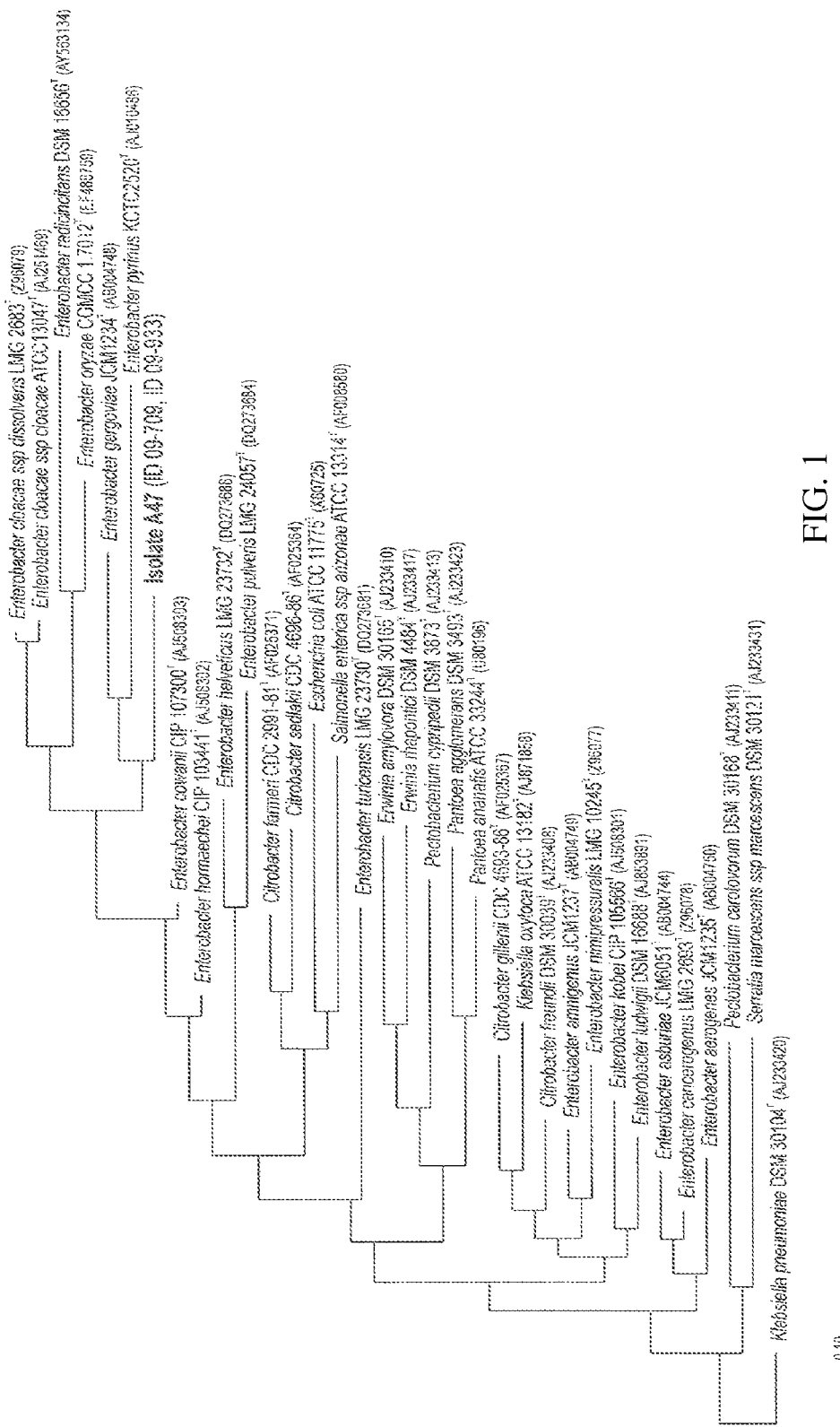
FIG. 1—Represents the phylogenetic dendrogram of the bacterium *Enterobacter* A47 (DSM 23139).

The fucose-containing polymer is obtained by cultivation of the bacterium *Enterobacter* A47 (DSM 23139). The microorganism may be a wildtype strain, a variant or a mutant, as long as it has the ability to synthesize the fucose-containing polymer. A pure culture may be used or, alternatively, one can use a mixed culture in which at least one microorganism is able to produce the polymer of the disclosed subject matter.

The preferred microorganism to obtain the polymer of the disclosed subject matter is the bacterium *Enterobacter* A47 (DSM 23139) with the characteristics described as follows. The biochemical and genetic characterization of the microorganism was performed by DSMZ (Deutsche Sammlung von Mikroorganismen and Zellkulturen GmbH).

1.1. Morphological Characterization of the Bacterium *Enterobacter* A47 (DSM 23139)

The bacterium *Enterobacter* A47 (DSM 23139) is a rod with the following dimensions: 0.7-0.8 µm×1.2-2.5 µm. It is a Gram negative motile bacterium.

1.2. Biochemical Profile of the Bacterium *Enterobacter* A47 (DSM 23139)

The bacterium *Enterobacter* A47 (DSM 23139) has the following biochemical profile, which is typical of the *Enterobacter* genus (Table 1):

TABLE 1

Biochemical profile of the bacterium *Enterobacter* A47 (DSM 23139) ("+" and "−" represent a positive or negative reaction, respectively, to the test preformed).

| Test | Result |
|---|---|
| Lysis by 3% KOH | + |
| Aminopeptidase (Cerny) | + |
| Catalase | + |

TABLE 1-continued

Biochemical profile of the bacterium *Enterobacter* A47 (DSM 23139) ("+" and "−" represent a positive or negative reaction, respectively, to the test preformed).

| Test | Result |
| --- | --- |
| Growth anaerobic | + |
| Gas from glucose | + |
| $H_2S$ | − |
| Indol | − |
| Methylred | − |
| Degradation of: | |
| Gelatine | − |
| Tween 80 | − |
| DNA | − |
| Urea | + |
| Citrat (Simmons) | + |
| Malonate utilization | + |
| VP | + |
| ONPG | + |
| ADH | + |
| LDC | − |
| ODC | + |
| Acid from (ASS): | |
| Glucose | + |
| Fructose | + |
| Mannose | + |
| Maltose | + |
| D-Xylose | + |
| Sucrose | + |
| Trehalose | + |
| L-Arabinose | + |
| Rhamnose | + |
| Galactose | + |
| Adonitol | + |
| Dulcitol | − |
| Erytritol | − |
| Inositol | − |
| Glicerol | + |

1.3. 16S rDNA Gene Sequence of the Bacterium *Enterobacter* A47 (DSM 23139)

The 16S rRNA gene sequence of the bacterium *Enterobacter* A47 (DSM 23139) (Table 2) was determined by direct sequencing of PCR-amplified 16S rDNA. Genomic DNA extraction, PCR (Polymerase Chain Reaction) mediated amplification of the 16S rDNA and purification of the PCR product was carried out as described by Rainey et al (1996). Purified PCR products were sequenced using the CEQ™DTCS-Quick Start Kit (Beckman Coulter) as directed in the manufacturer's protocol. Sequence reactions were electrophoresed using the CEQ™8000 Genetic Analysis System. The resulting sequence data was put into alignment editor ae2 (Maidak et al, 1999), aligned manually and compared with the representative 16S rRNA gene sequences of organisms belonging to the *Enterobacteriaeceae* (Maidak et al, 1999). For comparison 16S sequences were obtained from the EMBL, RDP or DSMZ databases.

TABLE 2

16S rDNA gene sequence of the bacterium *Enterobacter* A47 (DSM 23139)-SEQ ID NO 1

```
   1 TGATCCTGGC TCAGATTGAA CGCTGGCGGC AGGCCTAACA
     CATGCAAGTC GAACGGTAAC

61 AGGAAGCAGC TTGCTGCTTC GCTGACGAGT GGCGGACGGG
     TGAGTAATGT CTGGGAAACT

121 GCCTGATGGA GGGGGATAAC TACTGGAAAC GGTAGCTAAT
     ACCGCATAAY GTCGCAAGAC

181 CAAAGAGGGG GACCTTCGGG CCTCTTGCCA TCGGATGTGC
     CCAGATGGGA TTAGCTAGTA

241 GGTGGGGTAA CGGCTCACCT AGGCGACGAT CCCTAGCTGG
     TCTGAGAGGA TGACCAGCCA

301 CACTGGAACT GAGACACGGT CCAGACTCCT ACGGGAGGCA
     GCAGTGGGGA ATATTGCACA

361 ATGGGCGCAA GCCTGATGCA GCCATGCCGC GTGTATGAAG
     AAGGCCTTCG GGTTGTAAAG

421 TACTTTCAGC GGGGAGGAAG GCGATAAGGT TAATAACCTT
     GTCGATTGAC GTTACCCGCA

481 GAAGAAGCAC CGGCTAACTC CGTGCCAGCA GCCGCGGTAA
     TACGGAGGGT GCAAGCGTTA

541 ATCGGAATTA CTGGGCGTAA AGCGCACGCA GGCGGTCTGT
     CAAGTCGGAT GTGAAATCCC

601 CGGGCTCAAC CTGGGAACTG CATTCGAAAC TGGCAGGCTA
     GAGTCTTGTA GAGGGGGGTA

661 GAATTCCAGG TGTAGCGGTG AAATGCGTAG AGATCTGGAG
     GAATACCGGT GGCGAAGGCG

721 GCCCCTGGA CAAAGACTGA CGCTCAGGTG CGAAAGCGTG
     GGGAGCAAAC AGGATTAGAT

781 ACCCTGGTAG TCCACGCCGT AAACGATGTC GACTTGGAGG
     TTGTGCCCTT GAGGCGTGGC

841 TTCCGGAGCT AACGCGTTAA GTCGACCGCC TGGGGAGTAC
     GGCCGCAAGG TTAAAACTCA

901 AATGAATTGA CGGGGGCCCG CACAAGCGGT GGAGCATGTG
     GTTTAATTCG ATGCAACGCG

961 AAGAACCTTA CCTACTCTTG ACATCCAGAG AACTTTCCAG
     AGATGGATTG GTGCCTTCGG

1021 GAACTCTGAG ACAGGTGCTG CATGGCTGTC GTCAGCTCGT
     GTTGTGAAAT GTTGGGTTAA

1081 GTCCCGCAAC GAGCGCAACC CTTATCCTTT GTTGCCAGCG
     GTYAGGCCGG GAACTCAAAG

1141 GAGACTGCCA GTGATAAACT GGAGGAAGGT GGGGATGACG
     TCAAGTCATC ATGGCCCTTA

1201 CGAGTAGGGC TACACACGTG CTACAATGGC GCATACAAAG
     AGAAGCGACC TCGCGAGAGC

1261 AAGCGGACCT CATAAAGTGC GTCGTAGTCC GGATTGGAGT
     CTGCAACTCG ACTCCATGAA

1321 GTCGGAATCG CTAGTAATCG TGGATCAGAA TGCCACGGTG
     AATACGTTCC CGGGCCTTGT

1381 ACACACCGCC CGTCACACCA TGGGAGTGGG TTGCAAAAGA
     AGTAGGTAGC TTAACCTTCG

1441 GGAGGGCGCT TACCACTTTG TGATTCATGA CTGGGGTGAA
     GTCGTAACAA GGTAACCGTA

1501 GGGAACCTGC GGGCTGGATC ACC
```

1.4. Phylogenetic Dendrogram of the Bacterium *Enterobacter* A47 (DSM 23139)

The phylogenetic dendrogram of the bacterium *Enterobacter* A47 (DSM 23139) was constructed using the ARB package (Pruesse et al, 2007). Based on the evolutionary distance values, the phylogenetic tree was constructed by the neighbor-joining method (Jukes and Cantor, 1969), using the corrections of Saitou e Nei (1987). The root of the tree was determined by including the 16S rRNA gene sequence of *Klebsiella pneumoniae* into the analysis. The scale bar below the dendrogram indicates 1 nucleotide substitution per 100 nucleotides.

The 16S rDNA gene sequence of the bacterium *Enterobacter* A47 (DSM 23139) shows highest similarity with the bacteria *Enterobacter pyrinus* (98.3%), *Enterobacter hormaechei* (99.0%) and *Enterobacter asburiae* (98.9%). The criterion to identify a given microorganism within a known species is defined as having a similarity of at least >90% or, ideally, >99.5%, with the type strain for that species (Janda and Abbott, 2007).

In view of this, the microbial culture to be used in the process for the production of the polymer of the disclosed subject matter may be any microorganism that shares a similarity of at least 99.0±0.5% with SEQ ID NO 1 da *Enterobacter* A47 (DSM 23139), according to Table 2, obtained by genetic manipulation, mutation, variation or directly from Nature.

2. Characterization of the Process for the Production of the Polymer

The polymer of the presently disclosed subject matter is produced in a stirred aerated bioreactor, with pH and temperature control. The process for the production of the polymer is initiated by the inoculation of the microorganism in a nutrient aqueous medium containing a carbon source, a nitrogen source and inorganic salts. The process comprehends an initial batch phase, followed by a fed-batch phase, during which mineral medium is introduced into the bioreactor.

2.1. Cultivation Medium

The cultivation medium for the production of the fucose-containing polymer consists of a nutrient aqueous medium, containing a carbon source, a nitrogen source and inorganic salts.

2.1.1. Carbon Source

The preferred carbon source is glycerol and glycerol containing mixtures. Alternatively, the carbon source may be a monomeric, dimeric or olygomeric sugar, an alcohol, an organic acid, an alkane or mixtures containing two or more of the referred compounds.

The carbon source may also be food or industrial waste or byproduct, containing one or several of the compounds referred above, such as for example, glycerol byproduct from the biodiesel industry, sugar molasses, whey or olive oil wastes. Glycerol byproduct from the biodiesel industry is mainly composed by impure glycerol and containing variable amounts of methanol (5-50%), besides several other contaminants reminiscent from the industrial process (e.g. NaOH, fatoils, some esters, sulphur, proteins and minerals). Sugar molasses are a sugar refinery byproduct rich in sugars (sucrose, glucose and fructose) (>50%). Whey is a byproduct of the cheese industry, mainly composed by lactose. The organic fraction of olive oil wastes includes sugars, tannins, polyphenols, polyalcohols, pectins and lipids. Other food or industrial wastes and byproducts that have in their composition compounds such as sugars, alcohols, organic acids and/or lipids may be used as substrates for the microbial cultivation and production of the fucose-containing polymer.

In the process for the production of the fucose-containing polymer, according to the disclosed subject matter, the carbon source must represent between 2 and 10% (w/v) of the aqueous nutrient medium, during the batch phase, in order to adequately supply for cellular growth. During the following fed-batch phase, the carbon source should be kept above 0.1% (p/v), preferably above 0.5 (p/v), in order to guaranty carbon availability for polymer synthesis.

2.1.2. Nitrogen Source

The nitrogen source for the microbial cultivation may be an inorganic salt (e.g. $(NH_4)_2HPO_4$, $NH_4OH$, $(NH_4)_2SO_4$, $NH_4Cl$) or an organic nitrogen compound (e.g. urea, aminoacids), mixtures thereof or a food or industrial waste or byproduct containing nitrogen compounds (e.g. soya flour, yeast extract, wheat bran).

In the process for the production of the fucose-containing polymer the nitrogen source must have an initial concentration between 0.6 and 3.0 g/L, during the batch phase, such as to assure cellular growth. During the following fed-batch phase, the nitrogen source must be kept below 0.3 g/L, preferably below 0.1 g/L, thus creating a nitrogen limitation. Hence, during the fed-batch cellular growth is limited or restricted by nitrogen limitation that, concomitantly with the carbon availability, induces the synthesis of the fucose-containing polymer.

2.1.3. Inorganic Salts

The cultivation medium also includes, in traces amounts, metal cations, namely, sodium, potassium, magnesium, iron, manganese, cobalt, copper and zinc. Each of these cations must be present in the cultivation medium in concentrations between 0.001 and 100 mM, except sodium that may be present in higher amounts, especially for pH control.

2.2 Cultivation Conditions

The bioreactor cultivation is initiated by the inoculation of the microorganism in the aqueous nutrient medium described above, aerated with compressed air. The volume of inoculum should represent between 10 and 30% of the total reaction medium at the beginning of the cultivation.

Throughout the cultivation, the temperature is controlled between 15 and 45° C., preferable between 26 and 37° C., and the pH is controlled between 5.0 and 9.0, preferably between 6.5 and 7.0.

The dissolved oxygen concentration is high (>70%) at the beginning of the cultivation, gradually decreasing during the batch phase concomitant with the cellular growth. During the fed-batch phase the dissolved oxygen concentration is controlled below 30%, preferably below 10% or even under anaerobic conditions. The air flow rate may be kept constant between 0.1 and 2.0 vvm, being the dissolved oxygen concentration controlled by the automatic variation of the stirring speed between 0 and 2000 rpm, preferably between 400 and 800 rpm. Alternatively, the air flow rate may vary throughout the cultivation between 0 and 2.0 vvm, while keeping a constant stirring rate. The dissolved oxygen concentration during the fed-batch phase may also be controlled by substrate addition. In this case, both the stirring speed and the air flow rate may be kept constant at a value between 0 and 2000 rpm, and between 0 and 2.0 vvm, respectively.

Polymer synthesis is initiated during the batch phase but it occurs mainly during the fed-batch phase, when cellular growth slows down or stops due to the nitrogen limitation imposed to the bioreactor. During the fed-batch phase, nutrient medium is introduced into the bioreactor, which created conditions of carbon availability and nitrogen limitation. Nitrogen concentration in this phase is kept below 0.3 g N/L, preferably below 0.1 g N/L. Under these conditions, cellular growth is restricted and the polymer is produced as long as there is carbon available to match its consumption by the culture.

Polymer synthesis in the bioreactor may be kept for 4-7 days or until the moment when the broth becomes too viscous that it is no longer possible to maintain an homogeneous distribution of oxygen, temperature and nutrients. This situation occurs when the apparent viscosity of the broth reaches around 2.0 Pa·s (measured at 30° C., at a shear rate of 5 s$^{-1}$).

Alternatively, the production of the polymer of the disclosed subject matter may be kept in a continuous process or in a repeated fed-batch process. In the continuous process, the nutrient medium is continuously introduced in the bioreactor, being the broth containing the polymer also continuously removed. In the repeated fed-batch process, the bioreactor operation mode described above (an initial batch phase, followed by a fed-batch phase) is cyclically repeated. About 10-30% of the broth volume left is in the bioreactor and serves as the inoculum for the following cycle. These two alternative bioreactor operation modes allow for an optimization of the process, since non productive periods, namely, new inoculum and bioreactor preparation, are eliminated.

2.2. Extraction and Purification of Cultivation Products

The cultivation broth obtained at the end of the cultivation may be used directly, without any processing. Alternatively, the raw polymer may be obtained by drying the broth at a temperature up to 80° C. or by freeze drying.

Alternatively, a native form of the polymer may be recovered from the broth at the end of the cultivation preferably by precipitation, which may be achieved by the addition of a water miscible solvent in which the polymer is insoluble, such as for example an alcohol (e.g. ethanol, isopropanol) or a ketone (e.g. acetone). The fucose-containing polymer is precipitated by the addition of 1-3 volumes of precipitating agent for each liter of broth. The polymer co-precipitates with cells, proteins, salts and other broth components that are insoluble in the precipitating agent. The precipitated polymer may be dried at a temperature up to 80° C. or freeze dried. This native polymer, as well as the broth and the raw polymer described above, may be used in applications such as for example wastewater treatment or animal feed.

In an alternative extraction procedure, the polymer of the disclosed subject matter may be partially purified in a process that includes cell removal by centrifugation (10 000-20 000 rpm, 30-60 minutes), followed by the addition of a precipitating agent (1-3 liters of precipitating agent for each liter of broth). The precipitating agent may be any of the solvents referred above (e.g. ethanol, isopropanol, acetone).

The cultivation broth is highly viscous at the end of the cultivation, thus cell separation is facilitated by diluting it (addition of 1-4 liters of deionized water for each liter of broth) prior to centrifuging. The precipitated polymer may be dried at a temperature up to 80° C. or freeze dried. This semi-purified polymer may be used in several applications such as, for example, the agro-food, cosmetics, paper, paints or oil industries, among others.

A pure polymer may be obtained by additionally using one or more of the following methods:
1) Re-precipitation of the polymer from diluted semi-purified polymer aqueous solutions (0.1-5.0 g/L), being the degree of purity increased with the number of re-precipitations performed;
2) Sequential precipitation with different precipitating agents, namely, ethanol, acetone and/or isopropanol, or mixtures thereof, thus promoting the elimination of different contaminants soluble in each solvent;
3) Washing the semi-purified polymer with solvents in which the polymer is insoluble (e.g. hexane) but that solubilizes one or more of the contaminants;
4) Use of proteolythic enzymes (e.g. tripsin), addition of protein precipitating agents (e.g. trichloroacetic acid) or denaturation of proteinaceous materials by heating at temperatures between 60 and 80° C.;
5) Dialysis, ultrafiltration or diafiltration of aqueous semi-purified polymer solutions, with reduced concentrations (0.1-5.0 g/L), which results in a high degree of purity since the high molecular weight polymer is separated from all low molecular weight contaminants.

The pure polymer obtained with any of these procedures may be dried at a temperature up to 80° C. or freeze dried. The high degree of purity of this polymer allows its use in the food, pharmaceutical and cosmetic industries, among others.

Several different combinations of the referred methods may be used to extract/purify the fucose-containing polymer, according to the degree of purity and the specific application for which it is intended for.

3. Polymer Characterization 3.1. Composition

The polymer of the presently disclosed subject matter is constituted mainly by a high molecular weight polysaccharide ($10^6$-$10^7$), with a fucose content of at least 10% of the total sugar content. That polymer is also composed by glucose and galactose (20-70% and 10-40% of the total sugar content, respectively). The relative composition of the referred sugars in the polymer, fucose, galactose and glucose, is dependent on the cultivation time and on the bioreactor operating conditions.

Additionally, the polymer of this disclosed subject matter may also possess other neutral sugars in minor amounts (<5%), such as mannose, rhamnose, xylose, ribose, arabinose, glucuronic acid and/or glucosamine.

The referred polymer possesses as well non sugar components, namely acyl groups, which represent up to 25% of the polymer's dry weight. The main acyl groups detected were succinate, pyruvate and acetate.

Typically, acetate and pyruvate represent between 0.5 and 5% of the polymer's dry weight, while succinate is present in higher quantities, normally between 1 and 20%. The composition of the polymer of the disclosed subject matter in terms of each acyl group is dependent on the reactor operating conditions and on the time of cultivation. The presence of pyruvate and succinate residues confers an anionic character to the polymer. As a consequence, it is able to immobilize toxic metals, making possible its application on toxic metals removal (heavy metals and radionucleotides) from contaminated soils and water.

Depending on the extraction/purification method, the polymer obtained may contain, besides the fucose-containing polymer, other components present in the cultivation broth, namely proteins and inorganic compounds. The maximum content of these components was detected in the native polymer (15-30% of proteins and 25-40% of inorganic compounds), while the minimum amount (<1%) was detected in the purified polymer obtained by dialysis.

3.2. Polymer Average Molecular Weight

The average molecular weight of the purified polymer, determined by Gel Permeation Chromatography, is in the range of $10^6$-$10^7$. Normally, when the polymer production is initiated during the microbial growth phase, its average molecular weight is around $10^5$, increasing over time during the cultivation run up to a relatively constant value in the range of $10^6$-$10^7$.

3.3. Properties of the Polymer 3.3.1. Solubility

The polymer of the disclosed subject matter is not soluble in a wide range of organic solvents at ambient temperature, including acetone, isopropanol, DMSO, hexane, diethyl ether, xylene and tetrachloroethylene, among others. This characteristic of the polymer opens the possibility to its application in the preparation of solvent resistant membranes to be used in separation processes. However, it was observed that the polymer is soluble in some organic solvents, namely in tetrachloroethane.

The polymer of the disclosed subject matter is stable in contact with the organic solvents tested, maintaining its composition in terms of sugar constituents and acyl groups after being exposed to those solvents. In addition, the average molecular weight was also not affected.

3.3.2. Viscosity of Polymer Aqueous Solutions

Figure 2:
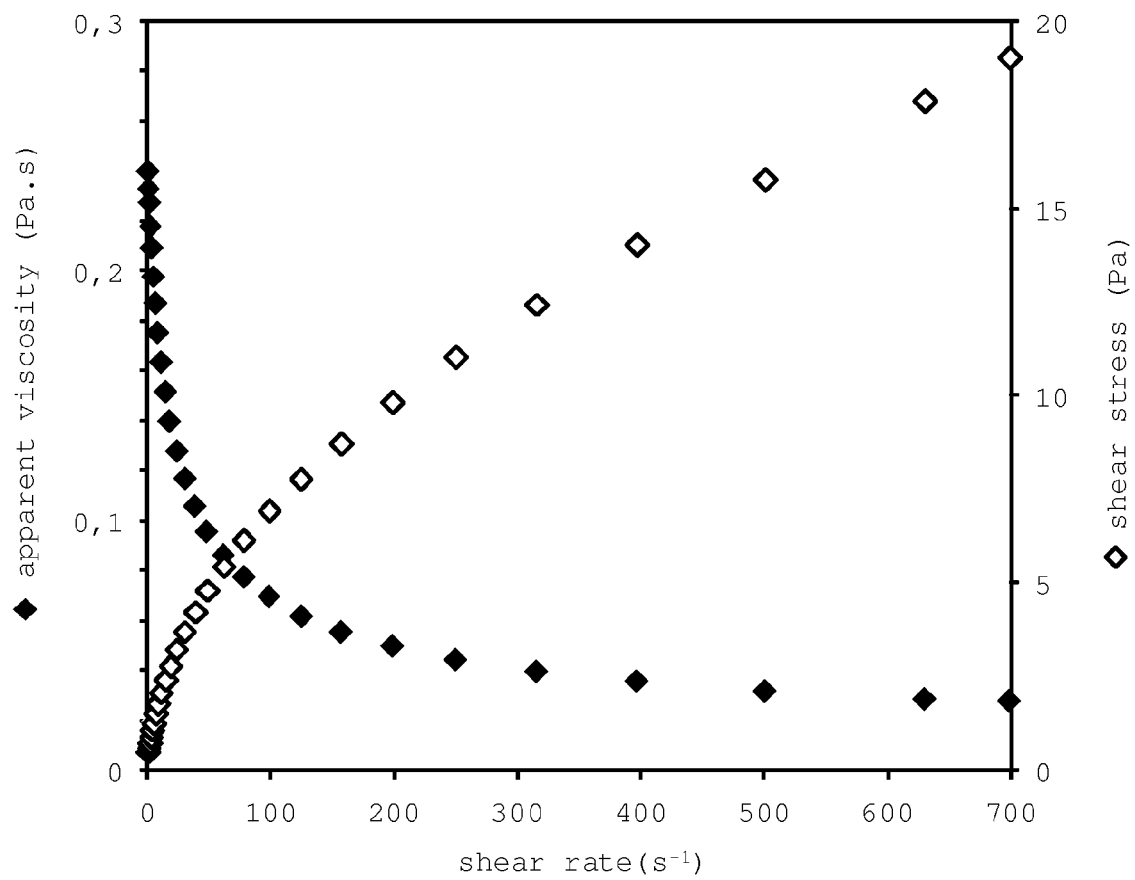
FIG. 2—Represents the apparent viscosity of an aqueous solution (0.8% w/v) of the fucose-containing polymer (measured at room temperature).

The aqueous solutions prepared with the polymer of the disclosed subject matter are not Newtonian fluids, presenting a pseudoplastic fluid behaviour (FIG. 2). The apparent viscosity of a 0.8% (w/v) polymer solution is 0.21 Pa·s measured at 25° C., for a shear rate of 5 $s^{-1}$, decreasing down to 0.02 Pa·s for a shear rate of 500 $s^{-1}$. Since the viscosity is immediately recovered when the shear rate is decreased, no hysteresis phenomena are observed. The pseudoplastic fluid behaviour of the polymer solutions confers this material the capacity of modifying the physical properties of aqueous systems, and the potential to be applied as thickener and texture enhancer, mainly in the food, pharmaceutical and cosmetic industries.

The apparent viscosity of the polymers aqueous solutions decreases with the increase of temperature, but the pseudoplastic fluid behaviour is maintained. The apparent viscosity of a 0.8% (w/v) polymer solution, measured at a shear rate of 5 $s^{-1}$ is 0.32 Pa·s at 15° C., decreasing to 0.05 Pa·s at 65° C.

The effect of sequential heating and cooling stages on the dynamic and steady-shear properties of the purified EPS solution was studied, performing cycles of consecutive heating and cooling steps. After recording the mechanical spectrum and the steady-state data at 25° C., the same sample was heated up to 40, 55, 70 and 80° C. It was observed that the apparent viscosity and dynamic moduli (G' and G"), recorded at 25° C. at the end of each cycle, were practically coincident. From this, we may conclude that the polymer sample is quite stable under temperature fluctuations, maintaining its properties in consecutive oscillatory and steady-state tests at 25° C., after being exposed to increasing temperatures up to 80° C. These characteristics let us think that the polymer may be used in aqueous formulations (e.g. food products) that are subjected to temperature fluctuations during processing.

Regarding the viscoelastic properties, the aqueous solutions of the polymer containing fucose present a behaviour of a viscous liquid (G">G' in the entire range of frequencies studied). No gel formation was detected under the conditions tested.

3.3.3. Emulsifying Activity

The polymer of the disclosed subject matter possesses emulsifying activity, which means that it is able to stabilize emulsions of water droplets in hydrophobic compounds, such as oils (e.g. olive oil, paraffin) and hydrocarbons (e.g. hexane, toluene). As so, the polymer may be used as bioemulsifier or stabilizing agent, and has the potential to replace synthetic emulsifiers in a wide range of applications, such as in the petroleum, detergent, textile, paper, paint, cosmetic, pharmaceutical and food industries.

The emulsifying activity is not confined to the purified polymer. Other forms, namely raw, native and semi-purified, have revealed the capacity of stabilizing emulsions of water in hydrophobic compounds. This ability was verified using solutions of polymer of the disclosed subject matter, with a concentration between 0.05 and 1.5%, when mixed with several hydrocarbons (e.g. hexadecane, hexane, toluene and xylene) and oils (olive oil and paraffin). The emulsions formed were quite stable for several weeks. Furthermore, they have shown to be very stable to temperature, resisting to heating from ambient temperature up to, 40, 50, 60 and 100° C.

3.3.4. Flocculating Activity

The polymer of the disclosed subject matter presents also a significant flocculating activity, and may be used as a natural bioflocculant agent. The flocculating agents are useful in the promotion of cell and colloid aggregation, being widely used in industrial applications, such as wastewater and drinking water treatment and food products. The biodegradability and safety of the polymer of the disclosed subject matter represent advantages over synthetic flocculants, which are dangerous for human health and whose degradation in the environment is difficult.

At ambient temperature and neutral pH, the flocculating activity of the polymer of the disclosed subject matter decreases from 70 to 60% with the increase of the polymer concentration from 0.1 to 0.8% (w/v). This flocculating activity was compared to that of commercial polysaccharides, namely, xanthan, alginate, Guar gum and carboxymethylcellulose. The polymer of the disclosed subject matter revealed to be a good flocculating agent, with a similar performance to that of commercial products, for the same polymer concentration.

3.3.5. Preparation of Biodegradable Films

The polymer containing fucose may be used to produce biodegradable composite films by mixing it with other biopolymers, such as starch, pectin, alginate, carrageenan, gluten, gellan and chitosan. These films may be applied as membranes in organic solvents processing and packaging materials.

Polysaccharides, such as chitosan, starch and guar gum, have been tested in the preparation of microspheres for drug controlled release. The polymer of this disclosed subject matter may be used as well for that purpose, either alone or mixed with other biopolymers.

4. Applications of the Polymer of the Presently Disclosed Subject Matter

The polymer of this disclosed subject matter presents emulsifying and flocculating activity, and forms high viscosity aqueous solutions with a pseudoplastic fluid behaviour. As a consequence, it may substitute other polysaccharides, like xanthan, alginate, guar gum and Arabic gum, in a wide range of applications, namely as a thickener, texture enhancer or binding agent, in the food, pharmaceutical and cosmetic industries.

The polymer containing fucose may be used to produce biodegradable composite films by mixing it with other biopolymers, such as starch, pectin, alginate, carrageenan, gluten, gellan and chitosan. These films may be applied as membranes in organic solvents processing (e.g. solvent dehydration by pervaporation), and in packaging materials, like food packaging, regarding their low permeability to gases (oxygen and carbon dioxide).

The polymer containing fucose may also be used as a source of oligosaccharides, obtained from the original polymer by applying physical treatments (e.g. microwaves, heat, irradiation and ultrasonication), chemical processes (e.g. acidic hydrolysis), enzymatic treatments (e.g. with hydrolases and liases) or biological processes (using microbial agents able to degrade de polymer and use all sugars as carbon source, except fucose). The obtained fucose and fuco-oligosaccharides, as well as the original polymer, isolated or mixed together, have a great potential in medical applications as anti-carcinogenic and anti-inflammatory agents, in the treatment of rheumatoid arthritis, to name a few (Vanhooren e Vandamme, 1999; Peterszegi et al, 2003b). Furthermore, due to the presence of fucose in its composition, the polymer of the disclosed subject matter has also a great potential to be used in cosmetics as hydrating and anti-ageing additive (Peterszegi et al, 2003a).

EXAMPLES

Example 1

Production of the Fucose-Containing Polymer by Cultivation of the Bacteria *Enterobacter* A47 (DSM 23139), Using Glycerol Byproduct from the Biodiesel Industry A culture of *Enterobacter* A47 (DSM 23139) was inoculated in 8 L of culture media with the composition presented in Table 3. The bioreactor (BioStat B-plus, Sartorius) was operated under the following conditions: controlled temperature at 30° C.; controlled pH at 6.80±0.05, automatic addition of NaOH 1 M and a constant aeration rate of 1.6 L/min (0.2 vvm). As microbial growth was taking place, the concentration of dissolved oxygen decreased from 80% saturation in the beginning of the cultivation run, to about 20% after 1 day.

From that instant, a continuous feed (of about 20 mL/h) was introduced in the reactor. Its composition was that presented in Table 3, but with a different glycerol concentration (200 g/L). These operating conditions limited the nitrogen concentration in the fermentation broth (below 0.1 g N/L) and permitted simultaneously a good availability of carbon source.

TABLE 3

Composition of the culture medium.

| componente | concentration |
|---|---|
| Glycerol co-product | 25 g/L |
| $K_2HPO_4$ | 5.8 g/L |
| $KH_2PO_4$ | 3.7 g/L |
| $(NH_4)_2HPO_4$ | 3.3 g/L |
| Mineral solution[(1)] | 1.0 mL/L |
| $MgSO_4$ 100 mM | 10 mL/L |

[(1)]composition of mineral solution (for 1 liter of HCl 1N): $FeSO_4·7H_2O$, 2.78 g; $MnCl_2·4H_2O$, 1.98 g; $CoSO_4·7H_2O$, 2.81 g; $CaCl_2·2H_2O$, 1.67 g; $CuCl_2·2H_2O$, 0.17 g; $ZnSO_4·7H_2O$, 0.29 g)

The dissolved oxygen concentration decreased gradually down to 10% saturation, value achieved after 2 days of cultivation. From that moment, it was controlled below 10% by automatic variation of the stirring rate between 400 and 800 rpm. After 1 day under these conditions, the viscosity of the fermentation broth increased quickly, which was related to polymer production.

Figure 3:
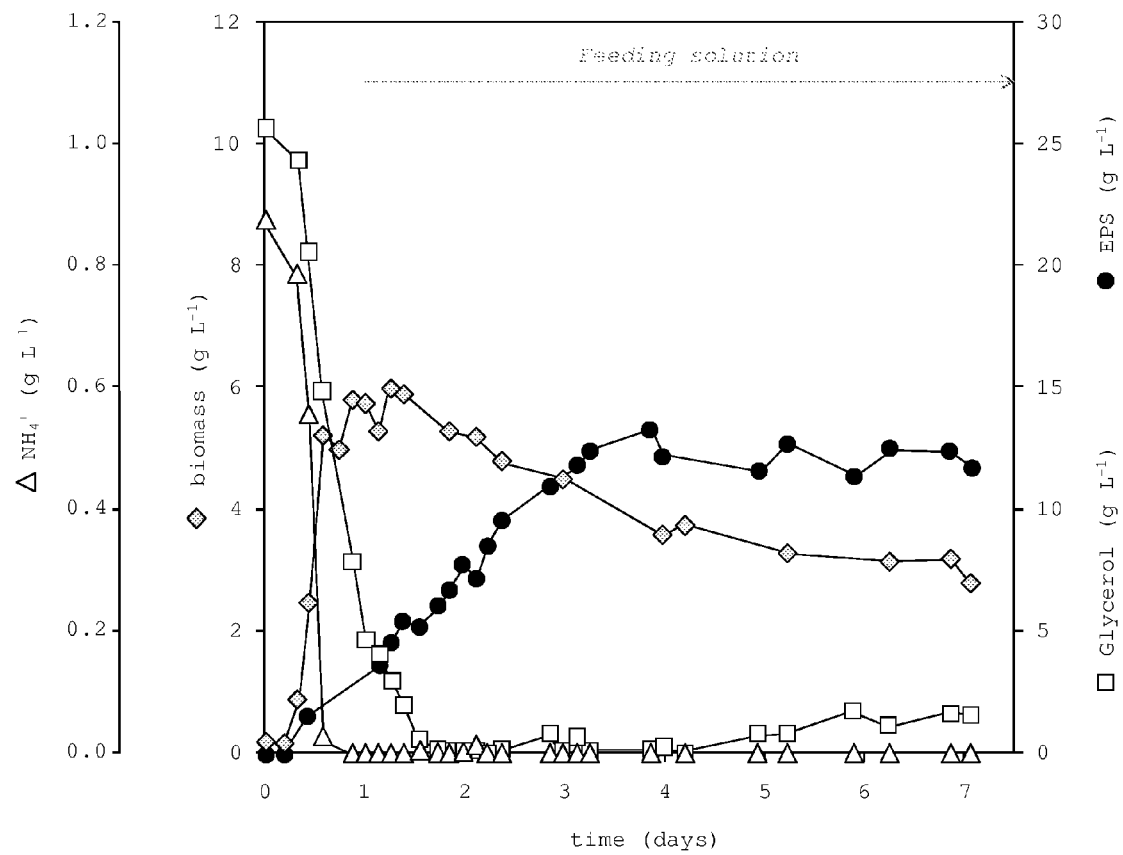
FIG. 3—Represents the time course of the consumption of the carbon source (glycerol) and nitrogen source (ammonium), the production of biomass and fucose-containing EPS, during the cultivation process for the production of the polymer of the disclosed subject matter.

At the end of 4 days of cultivation, the polymer concentration was nearly 13.3 g/L, which refers to polymer extracted and quantified in his semi-purified form (FIG. 3). The viscosity of the fermentation broth increased significantly between day 4 and day 7, even though the polymer production has ceased. The productivity reached the value of 3.6 g $L^{-1}$ $day^{-1}$ and the yield from glycerol was 0.47 g $g^{-1}$, considering the time interval in which polymer production took place (from day 1 to day 4).

The cultivation run was stopped at day 7, when the viscosity of the fermentation broth reached 3.0 Pa·s, at a shear rate of 5 $s^{-1}$ and T=30° C.

Example 2

Extraction and Purification of the Fucose-Containing Polymer Produced by *Enterobacter* A47 (DSM 23139) from Glycerol Byproduct In the end of the cultivation run described in Example 1, the polymer containing fucose was recovered from the fermentation broth, in the form of three different products with diverse purity grades: native, semi-purified and purified polymer.

The native polymer was obtained by the addition of acetone directly to the fermentation broth (3:1). The concentration of native polymer was 20.6 g/L.

To obtain the semi-purified polymer, the fermentation broth was firstly diluted to reduce viscosity (2 L of deionised water to 1 L of fermentation broth) and then the biomass was separated by centrifugation (20000 rpm, 30 min). Afterwards the cell-free supernatant was added slowly to acetone (1:3) under mild stirring, promoting the polymer precipitation. The precipitate was dissolved in deionised water and freeze-dried. The concentration of semi-purified polymer was 11.6 g/L.

In order to obtain the purified polymer, an aqueous solution of semi-purified polymer was processed by dialysis in contact with deionised water during 24 h, using a 3500 MWCO membrane (SnakeSkin™ Pleated Dialysis Tubing 68035—Thermo Scientific). Sodium azide was added (6 ppm) to prevent microbial degradation of the polymer. After that, the polymer was precipitated by adding acetone, redissolved in water and freeze-dried. The concentration of purified polymer was 5.5 g/L.

As an alternative, the polymer may be extracted/purified by the following methodology: dilution of the fermentation broth and biomass separation by centrifugation; heating at 60° C. for 1 h to inactivate the enzymes present in the supernatant that may be responsible by partial polymer degradation; dialysis of the supernatant in contact with deionised water and finally freeze-drying. With this method where recovered 5.0 g/L of purified polymer.

Example 3

Chemical Analysis of the Fucose-Containing Polymer Produced by *Enterobacter* A47 (DSM 23139)

The polymer produced as described in Example 1 and extracted as described in Example 2 was characterized in terms of its chemical composition, namely regarding its sugar composition, the content of acyl groups and the amount of non-sugar residues (proteins and ashes), using the methods described in Freitas et al (2009). The chemical composition of all polymer purity grades (native, semi-purified and purified by dialysis) was analysed over time, during the cultivation run.

After 1 day of cultivation the polymer was constituted mainly by glucose (77%) and galactose (15%), with lower amounts of fucose (6%). As the cultivation proceeded, the relative proportion of these sugar monomers has changed significantly: the glucose content decreased gradually to 40% at day 4, and the relative amount of galactose and fucose increased up to 26% and 28%, respectively.

The sugar composition was practically constant in the last 3 days of operation (glucose, 40-44%; fucose, 26-30%; galactose, 28-29%).

It was also observed a variation of the relative proportion of the acyl groups over time: it varied from 2.4% succinate, 0.2% pyruvate and 0.3% acetate, at day 1, to 20% succinate, 2.4% pyruvate and 2.0% acetate at day 4. Afterwards, at day 7 was observed a decrease of succinate content to 3.9%, along with an increase of pyruvate (4.9%) and acetate (3.6%).

The composition in terms of sugar and acyl groups constituents is similar for the different purity grade polymers. The same does not happen for the case of proteins and ashes. The content of these components decreases from the native to the semi-purified polymer, and from the later to the purified polymer.

Example 4

Production of the Fucose-Containing Polymer by Cultivation of the Bacteria Enterobacter A47 (DSM 23139), Using Glycerol Byproduct from the Biodiesel Industry, Under Different Temperatures and pH The culture Enterobacter A47 (DSM 23139) was cultivated in 2 L bioreactors, as described in example 1, except for temperature and pH that were controlled under different values, according to Table 4. At the end of each run, the polymer was recovered as described in example 2.

TABLE 4

Values of temperature and pH tested.

| Run | Temp (° C.) | pH | $\mu$ ($h^{-1}$) | $X_{max}$ (g/L) | $EPS_{max}$ (g/L) | $r_P$ (g/L · d) | $Y_{P/S}$ (g · $g^{-1}$) |
|---|---|---|---|---|---|---|---|
| 1 | 30.0 | 7.0 | 0.30 | 7.14 | 8.37 | 5.00 | 0.17 |
| 2 | 30.0 | 7.0 | 0.32 | 7.58 | 10.13 | 4.94 | 0.21 |
| 3 | 20.0 | 6.0 | 0.14 | 7.41 | 0.82 | 0.19 | 0.01 |
| 4 | 40.0 | 6.0 | 0.34 | 9.20 | 2.59 | 0.81 | 0.03 |
| 5 | 20.0 | 8.0 | 0.13 | 8.39 | 4.40 | 2.54 | 0.10 |
| 6 | 40.0 | 8.0 | 0.22 | 5.63 | 1.62 | 1.34 | 0.04 |
| 7 | 15.9 | 7.0 | 0.08 | 8.17 | 1.12 | 0.33 | 0.02 |
| 8 | 44.1 | 7.0 | — | 0.21 | 0.23 | 0.06 | 0.02 |
| 9 | 30.0 | 5.6 | 0.10 | 10.62 | 7.50 | 2.05 | 0.09 |
| 10 | 30.0 | 8.4 | 0.07 | 3.01 | 2.67 | 2.38 | 0.09 |

The conditions that maximize cell growth, polymer production and productivity were found to be temperatures between 25 and 34° C., and pH controlled between 6.5 and 7.5 (Table 5). In addition, within these temperature and pH ranges, the polymer's content in fucose was maximal. Outside these ranges, the culture has synthesized polymers with different composition, such as, for example: reduction of the fucose content (<14%), concomitant with an increase of the glucose content (>50%) and the addition of new monomers (e.g. rhamnose and glucosamine) as main components (up to 20% and up to 10%, respectively). Glucuronic acid was also detected in these polymers with a content up to 15%. The acyl groups content was also affected by temperature and pH during cultivation, being reduced to levels below 10% of the polymers' dry mass.

REFERENCES

Canilha L, Silva D D V, Carvalho W, Mancilha M (2005) Revista Analytica 20, 332-341.

Ç elik E, Ozbay N, Oktar N, Ç alik P (2008) Ind Eng Chem Res 47, 2985-2990.

Freitas F, Alves V D, Carvalheira M, Costa N, Oliveira R, Reis M A M (2009) Carbohydr Pol 78, 549-556.

Guetta O, Mazeau K, Auzely R, Milas M, Rinaudo M (2003a) Biomacromol 4, 1362-1371.

Guetta O, Milas M, Rinaudo M (2003b) Biomacromol 4, 1372-1379.

Janda J M, Abbot S L (2007) J Clin Microbiol 45(9), 2761-2764.

Joseleau J P, Marais M F (1979) Carbohydr Res 77, 183-190.

Jukes T H, Cantor C R (1969) In Mammalian protein metabolism, N Munro, Academic Press, New York, pp 21-132.

Kumar A S, Mody K, Jha B (2007) J Basic Microbiol 47, 103-117.

Kumar A S, Mody K (2009) Microbial Production of Biopolymers and Polymer Precursors—Applications and Perspectives. Caister Academic Press, Chapter 10.

Maidak B L, Cole J R, Parker C T, Garrity G M, Larsen N, Li B, Lilburn T G, McCaughey M J Olsen G J, Overbeek R, Pramanik S, Schmidt S, Tiedje J M, Woese C R (1999) Nucl Acids Res 27, 171-173.

Moreno J, Vargas M A, Olivares H, Rivas J, Guerrero M G (1998) J Biotechnol 60, 175-182.

Péterszegi G, Isnard N, Robert A M, Robert L (2003a) Biomedicine Pharmacotherapy 57, 187-194.

Péterszegi G, Fodil-Bourahla I, Robert A M, Robert L (2003b) Biomedicine Pharmacotherapy 57, 240-245.

Pruesse E, Quast C, Knittel, Fuchs B, Ludwig W, Peplies J, Glockner F O (2007) Nucl Acids Res 35, 7188-7196.

Rainey F A, W-R N, Kroppenstedt R M, Stackenbrandt E (1996) Int J Sys Bacteriol 46, 1088-1092.

Saitou N, Nei M (1987) Mol Biol Evol 4, 406-425.

Sutherland I W (2001) Int Dairy J 11, 663-674.

van den Bulk R W, Zevenhuizen L P T M, Cordewener J H G, Dons J J M (1991) Phytopathol 81(6), 619-623.

Vanhooren P T, Vandamme E J (1999) J Chem Technol Biotechnol 74, 479-497.

The invention claimed is:

1. A composition of purified fucose-containing polysaccharide wherein the fucose-containing polysaccharide comprises
    a) an amount of fucose which is at least 10% of the total carbohydrate content of the fucose-containing polysaccharide;
    b) acyl groups in an amount up to 25% of the dry weight of the polysaccharide, wherein the acyl groups comprise succinate, pyruvate, and acetate, and wherein the amount of pyruvate is up to 5% of the dry weight of the fucose-containing polysaccharide; and
    c) an amount of glucose which is between 20-70% of the total carbohydrate content of the fucose-containing polysaccharide.

2. The composition of claim 1, wherein the amount of acetate is up to 5% of the dry weight of the fucose-containing polysaccharide.

3. The composition of claim 1, wherein the amount of pyruvate is 0.5% to 5% of the dry weight of the fucose-containing polysaccharide.

4. The composition of claim 1, wherein the amount of succinate is 1% to 20% of the dry weight of the fucose-containing polysaccharide.

5. The composition of claim 1, further comprising mannose, rhamnose, xylose, ribose, arabinose, glucuronic acid, glucosamine, or a combination thereof in an amount which is less than 5% of the total carbohydrate content of the fucose-containing polysaccharide.

6. The composition of claim 1, wherein the average molecular weight of the polysaccharide is $10^6$-$10^7$ daltons as determined by gel permeation chromatography.

7. The composition of claim 1, further comprising an amount of galactose which is between 10-40% of the total carbohydrate content of the fucose-containing polysaccharide.

8. An emulsion comprising the composition of claim 1 and a hydrophobic compound.

9. A biodegradable composite film comprising the composition of claim 1.

10. The biodegradable composite film of claim 9, further comprising starch, pectin, alginate, carrageenan, gluten, gellan, chitosan, or a combination thereof.

11. A thickener comprising the composition of claim 1.

12. A texture enhancer comprising the composition of claim 1.

13. A binding agent comprising the composition of claim 1.

14. A flocculating agent comprising the composition of claim 1.

15. A pharmaceutical composition comprising the composition of claim 1.

16. A cosmetic comprising the composition of claim 1.

17. A microsphere for drug controlled release comprising the composition of claim 1.

* * * * *

SEQUENCE LISTING

<160> NUMBER OF SEQ ID NOS: 1

<210> SEQ ID NO 1

```
<211> LENGTH: 1523
<212> TYPE: DNA
<213> ORGANISM: Enterobacter sp.

<400> SEQUENCE: 1
tgatcctggc tcagattgaa cgctggcggc aggcctaaca catgcaagtc gaacggtaac      60
aggaagcagc ttgctgcttc gctgacgagt ggcggacggg tgagtaatgt ctgggaaact     120
gcctgatgga gggggataac tactggaaac ggtagctaat accgcataay gtcgcaagac     180
caaagagggg gaccttcggg cctcttgcca tcggatgtgc ccagatggga ttagctagta     240
ggtggggtaa cggctcacct aggcgacgat ccctagctgg tctgagagga tgaccagcca     300
cactggaact gagacacggt ccagactcct acggaggca gcagtgggga atattgcaca      360
atgggcgcaa gcctgatgca gccatgccgc gtgtatgaag aaggccttcg ggttgtaaag     420
tactttcagc ggggaggaag gcgataaggt taataacctt gtcgattgac gttacccgca     480
gaagaagcac cggctaactc cgtgccagca gccgcggtaa tacggagggt gcaagcgtta     540
atcggaatta ctgggcgtaa agcgcacgca ggcggtctgt caagtcggat gtgaaatccc     600
cgggctcaac ctgggaactg cattcgaaac tggcaggcta gagtcttgta gaggggggta     660
gaattccagg tgtagcggtg aaatgcgtag agatctggag gaataccggt ggcgaaggcg     720
gccccctgga caaagactga cgctcaggtg cgaaagcgtg gggagcaaac aggattagat     780
accctggtag tccacgccgt aaacgatgtc gacttggagg ttgtgccctt gaggcgtggc     840
ttccggagct aacgcgttaa gtcgaccgcc tggggagtac ggccgcaagg ttaaaactca     900
aatgaattga cgggggcccg cacaagcggt ggagcatgtg gtttaattcg atgcaacgcg     960 aagaaccta cctactcttg acatccagag aactttccag agatggattg gtgccttcgg    1020
gaactctgag acaggtgctg catggctgtc gtcagctcgt gttgtgaaat gttgggttaa    1080
gtcccgcaac gagcgcaacc cttatccttt gttgccagcg gtyaggccgg gaactcaaag    1140
gagactgcca gtgataaact ggaggaaggt ggggatgacg tcaagtcatc atggccctta    1200
cgagtagggc tacacacgtg ctacaatggc gcatacaaag agaagcgacc tcgcgagagc    1260
aagcggacct cataaagtgc gtcgtagtcc ggattggagt ctgcaactcg actccatgaa    1320
gtcggaatcg ctagtaatcg tggatcagaa tgccacggtg aatacgttcc cgggccttgt    1380
acacaccgcc cgtcacacca tgggagtggg ttgcaaaaga agtaggtagc ttaaccttcg    1440
ggagggcgct taccactttg tgattcatga ctggggtgaa gtcgtaacaa ggtaaccgta    1500
gggaacctgc ggctggatc acc                                            1523
```